United States Patent
Carstens

(10) Patent No.: US 7,144,429 B2
(45) Date of Patent: Dec. 5, 2006

(54) SEAL ARRANGEMENT FOR RESIDUAL LIMB PROSTHETIC SOCKET

(75) Inventor: Felix Carstens, Neustadt an der Weinstrasse (DE)

(73) Assignee: Ossur, HF, Reykjavik (IS)

( * ) Notice: Subject to any disclaimer, the term of this patent is extended or adjusted under 35 U.S.C. 154(b) by 412 days.

(21) Appl. No.: 10/487,926

(22) PCT Filed: Aug. 23, 2002

(86) PCT No.: PCT/DE02/03084

§ 371 (c)(1),
(2), (4) Date: Feb. 27, 2004

(87) PCT Pub. No.: WO03/024367

PCT Pub. Date: Mar. 27, 2003

(65) Prior Publication Data

US 2004/0243252 A1    Dec. 2, 2004

(30) Foreign Application Priority Data

Aug. 30, 2001 (DE) ................. 101 42 491

(51) Int. Cl.
*A61F 2/80* (2006.01)
(52) U.S. Cl. ........................................................ 623/34
(58) Field of Classification Search .................. 623/34, 623/35–38, 33; 602/62–64
See application file for complete search history.

(56) References Cited

U.S. PATENT DOCUMENTS

| 980,457 A | 1/1911 | Toles |
| 1,398,824 A | 11/1921 | Abrams |
| 1,893,853 A | 1/1933 | Tullis |
| 2,530,285 A | 11/1950 | Catranis .................... 3/3 |
| 2,533,404 A | 12/1950 | Sharp et al. ................ 3/9 |
| 2,634,424 A | 4/1953 | O'Gorman .................. 3/20 |
| 2,671,225 A | 3/1954 | Schoene et al. ............ 3/19 |
| 2,808,593 A | 10/1957 | Andersen .................... 3/17 |
| 3,393,407 A | 7/1968 | Kandel ....................... 3/20 |
| 3,671,980 A | 6/1972 | Baird .......................... 3/20 |
| 4,923,474 A | 5/1990 | Klasson et al. ........... 623/33 |
| 5,007,937 A | 4/1991 | Fishman et al. .......... 623/34 |
| 5,139,523 A | 8/1992 | Paton et al. ............... 623/37 |
| 5,163,965 A | 11/1992 | Rasmusson et al. ...... 623/36 |
| 5,226,918 A | 7/1993 | Silagy et al. ............. 623/32 |
| 5,314,496 A | 5/1994 | Harris et al. ............. 623/31 |
| 5,376,129 A | 12/1994 | Faulkner et al. ......... 623/33 |
| 5,376,131 A | 12/1994 | Lenze et al. ............. 623/34 |
| 5,549,709 A | 8/1996 | Caspers .................... 623/24 |
| 5,658,353 A | 8/1997 | Layton ..................... 623/34 |
| 5,702,489 A | 12/1997 | Slemker ................... 623/34 |
| 5,718,925 A | 2/1998 | Kristinsson et al. ...... 425/2 |
| 5,728,170 A | 3/1998 | Becker et al. ............ 623/37 |
| 5,735,906 A | 4/1998 | Caspers .................... 623/34 |
| 5,888,216 A | 3/1999 | Haberman ................ 623/36 |

(Continued)

FOREIGN PATENT DOCUMENTS

DE    745 981    12/1943

(Continued)

*Primary Examiner*—Alvin J. Stewart
(74) *Attorney, Agent, or Firm*—Bacon & Thomas, PLLC

(57) ABSTRACT

A prosthetic socket seal includes at least one radially projecting sealing lip which jointly with a base subtends an annular gap. This annular gap is vented on a proximal side by the external atmosphere, resulting in creation of a pressure gradient at the sealing lip that produces stronger compression of the sealing lip against the prosthetic socket with increasing partial vacuum on a distal side of the sealing lip.

16 Claims, 4 Drawing Sheets

U.S. PATENT DOCUMENTS

| | | | |
|---|---|---|---|
| 5,904,722 A | 5/1999 | Caspers | 623/34 |
| 5,931,872 A | 8/1999 | Lohmann | 623/36 |
| 5,972,036 A | 10/1999 | Kristinsson et al. | 623/33 |
| 6,149,691 A | 11/2000 | Fay et al. | 623/37 |
| 6,231,616 B1 | 5/2001 | Helmy | 623/34 |
| 6,231,617 B1 | 5/2001 | Fay | 623/36 |
| 6,273,918 B1 | 8/2001 | Yuhasz et al. | 623/33 |
| 6,287,345 B1 | 9/2001 | Slemker et al. | 623/34 |
| 6,361,568 B1 | 3/2002 | Hoerner | 623/32 |
| 6,508,842 B1 | 1/2003 | Caspers | 623/32 |
| 6,554,868 B1 | 4/2003 | Caspers | 623/34 |
| 6,585,774 B1 | 7/2003 | Dean, Jr. et al. | 623/37 |
| 6,645,253 B1 | 11/2003 | Caspers | 623/26 |
| 6,726,726 B1 | 4/2004 | Caspers | 623/34 |
| 6,761,742 B1 | 7/2004 | Caspers | 623/34 |
| 2001/0005798 A1 | 6/2001 | Caspers | 623/34 |
| 2001/0016781 A1 | 8/2001 | Caspers | 623/34 |
| 2002/0040248 A1 | 4/2002 | Karason | 623/37 |
| 2002/0087215 A1 | 7/2002 | Caspers | 623/34 |
| 2002/0091449 A1 | 7/2002 | Caspers et al. | 623/34 |
| 2002/0099450 A1 | 7/2002 | Dean, Jr. et al. | 623/26 |
| 2003/0191539 A1 | 10/2003 | Caspers | 623/35 |
| 2004/0030411 A1 | 2/2004 | Caspers | 623/37 |
| 2004/0098136 A1 | 5/2004 | Caspers | 623/34 |
| 2004/0122528 A1 | 6/2004 | Egilsson | 623/34 |
| 2004/0143345 A1 | 7/2004 | Caspers | 623/36 |
| 2004/0167638 A1 | 8/2004 | Caspers | 623/27 |
| 2004/0181290 A1 | 9/2004 | Caspers | 623/34 |
| 2004/0236434 A1 | 11/2004 | Carstens | 623/34 |
| 2004/0243251 A1 | 12/2004 | Carstens | 623/34 |
| 2004/0243252 A1 | 12/2004 | Carstens | 623/34 |

FOREIGN PATENT DOCUMENTS

| | | |
|---|---|---|
| DE | 813190 | 7/1951 |
| EP | 631 765 | 2/1998 |
| GB | 267988 | 3/1927 |
| GB | 2 069 847 | 9/1981 |
| GB | 2 087 727 | 6/1982 |
| WO | 00/74611 A2 | 12/2000 |
| WO | 01/54631 A1 | 8/2001 |
| WO | 03/024367 A2 | 3/2003 |
| WO | 03/024370 A1 | 3/2003 |
| WO | 03/039398 A2 | 5/2003 |
| WO | 03/099173 A1 | 12/2003 |

SEAL ARRANGEMENT FOR RESIDUAL LIMB PROSTHETIC SOCKET

BACKGROUND OF THE INVENTION

A. Field

This invention relates to hermitic seal arrangements between residual limbs and vacuum retained prosthetic sockets.

B. Related Art

Residual limbs of amputees are inserted like a piston in a cup-shaped prosthetic sockets. Thus, it is known to utilize atmospheric air pressure (or partial vacuum) to retain such prosthetic sockets on residual limbs. A residual limb for this purpose must be kept hermetically sealed against the inner prosthetic socket wall or against a liner pulled over the residual limb.

With proper sealing, a force tending to remove the prosthetic socket from the residual limb will generate a partial vacuum that reacts against the force. On the other hand the retention force collapses immediately when air enters a gap between the residual limb and the prosthetic socket.

The European patent application EP 0 632 765 discloses a prosthetic socket fitted with a seal which maintains sealing between the residual limb and the prosthetic socket.

For that purpose the prosthetic socket is fitted with a peripheral groove located a distance from its distal end and which receives a sealing ring. The sealing ring consists of an annular core covered with a layer of elastomer. A sealing lip is formed on said ring and extends toward the inside area of the prosthetic socket.

The purpose of the sealing lip—which hugs the skin of the residual limb is to compensate for the diameter fluctuations of the residual limb. Because the prosthetic socket is made of a rigid material, its inside diameter is constant. On the other hand, the residual limb volume changes over the long-term and the short-term. The long-term fluctuations are caused by changes in tissue volume, whereas the short-term fluctuations depend on the residual limb's blood pressure and circulation within the residual limb. It is known that at higher temperatures the extremities tend to swell while at low temperatures their diameters shrink. This phenomenon may be observed for instance even in a healthy individual at his watch band.

The lip seal is folded toward the closed prosthetic socket end when the patient inserts a residual limb into the prosthetic socket. The lip seal will then rest against the residual limb solely on account of being prestressed.

The moment a force is applied to remove the prosthetic socket from the residual limb, a slight partial vacuum is set up between the residual limb and the prosthetic socket space between the distal end and the lip seal. The magnitude of the said partial pressure is approximately proportional to the extent of the annular gap between the residual limb and the prosthetic socket.

With respect to the prior art, the pressure difference at the lip seal is in a direction lifting said lip seal from the residual limb, thereby allowing air to enter the annular gap and, on account of the ensuing loss of partial vacuum, retention is lost.

The magnitude of the admissible partial vacuum at which the sealing lip would detach depends on the radial prestressing force by which the sealing lip rests against the residual limb. It is observed that a comparatively large prestressing force is required, which in turn may entail interference in the blood circulation in the region between the sealing lip and the distal end of the residual limb.

Accordingly, the objective of the present invention is to create a seal the sealing effect of which is substantially independent of a prestressing force magnitude.

SUMMARY OF THE INVENTION

In this new seal, a base is seated on the residual limb.

A sealing lip originates at the base and at its edge points proximally. When the residual limb jointly with said seal has been inserted into a cup-shaped prosthetic socket—which is air tight in the region between the sealing lip and the distal end—a partial vacuum will arise as soon as a force tending to remove the prosthetic socket from the residual limb has been applied, If the sealing lip should enclose the residual limb discontinuously, then the end of this sealing lip should be bonded to the base.

Means associated with the sealing arrangement ventilates the rear of the sealing lip to ambient air pressure, so that atmospheric pressure prevails at the sealing lip between it and the residual limb. The opposite side of the sealing lip resting against the inside wall surface of the prosthetic socket is exposed to the more or less partial vacuum in said socket.

Accordingly, a pressure gradient exists at the sealing lip and the direction of the gradient is such that it will increasingly press the sealing lip against the prosthetic socket inner wall as the partial vacuum increases and thereby will improve air tightness.

As regards the new seal, the sealing effect is independent of the magnitude of the initial force pressing the sealing lip against the prosthetic socket. Self-reinforcing compression is at work the moment the partial vacuum in the prosthetic socket increases. Air leaks therefore cannot occur on the base side.

The base may be made sufficiently large in the residual limb longitudinal direction such that excellent air tightness shall be attained even with low compression forces.

The compression applied to the residual limb may be decreased by fitting the seal at the base with at least one other sealing lip running in the same direction as the seal which seals off the prosthetic socket, the former sealing lip being primarily configured to seal off the said residual limb. Again, the gap between the two sealing lips is back-vented in order to provide atmospheric pressure between them.

A cuff-shaped base running above the root of the sealing lip which seals against the prosthetic socket operates as a second sealing lip and extends proximally over the root of said sealing lip. The support itself acts as a second sealing lip which is flexible enough to follow the local contours. As a result a small prestressing force may be used without degrading the air tightness relative to the residual limb and the prosthetic socket.

In order not to degrade the air tightness, the particular sealing lips are adequately stretchable in the residual limb peripheral direction.

Another way to retain the sealing lip against the prosthetic socket even when a definite gap arises on account of residual limb volume changes between the residual limb and the prosthetic socket, is to use magnetic particles in the sealing lip and ferromagnetic particles in the prosthetic socket. In the manner of a magnetic locking means, the sealing lip automatic will be drawn to the prosthetic socket.

The magnetized particles may be present selectively in the prosthetic socket or in the sealing lip while the other component may contain unmagnetized, ferromagnetic particles.

The sealing lip base selectively may be a separate cuff directly worn on the skin or on an external, appropriate liner, or the cuff may be formed of the liner itself.

The back-venting means may be a simple annular groove running along the sealing lip and configured in such a way that even in the most adverse case its opening will be maintained and the sealing lip will be vented by the external atmosphere by means of a pressure compensating duct in the cuff or in the liner.

The back-venting means simultaneously may also be used to keep the sealing lip spaced from the base or liner, for instance when the seal is used for a residual limb containing low-resiliency tissue, for instance in the case of below-knee prostheses. The back venting spacer assures that even in the event of volume loss, the sealing lip shall rest on account of its basic prestressing force against the inside wall surface of the prosthetic socket. In this manner prosthetic sockets may be used that may be fitted immediately following surgery, that is before the residual limb has shrunk. The loss of volume normally would entail leakage, which however the new seal easily precludes.

For such a purpose, the spacers shall be advantageously compressible and air-permeable in order not to interfere with back venting. Open-cell foam is an appropriate material for this purpose.

Another way to attain the required prestressing force is to impart a basic prestressing force to the sealing lip pointing toward the socket in such manner that the sealing edge automatically adjusts itself to a cross-section exceeding that defining the root.

Another objective of the present invention is to create a prosthetic socket both able to cooperate with the seal and containing ferromagnetic particles in its sealing lip facing the prosthetic socket.

In this design the socket also contains ferromagnetic particles which may be selectively magnetized or not in order to tightly attract the sealing lip against the inside wall surface of the prosthetic socket.

Other features of the present invention are recited in the dependent claims. Moreover combinations of features for which no explicit illustrative embodiment is offered herein also shall be construed as being claimed.

DESCRIPTION OF THE DRAWINGS

The appended drawing show illustrative embodiments of the present invention.

DETAILED DESCRIPTION

Figure 1:
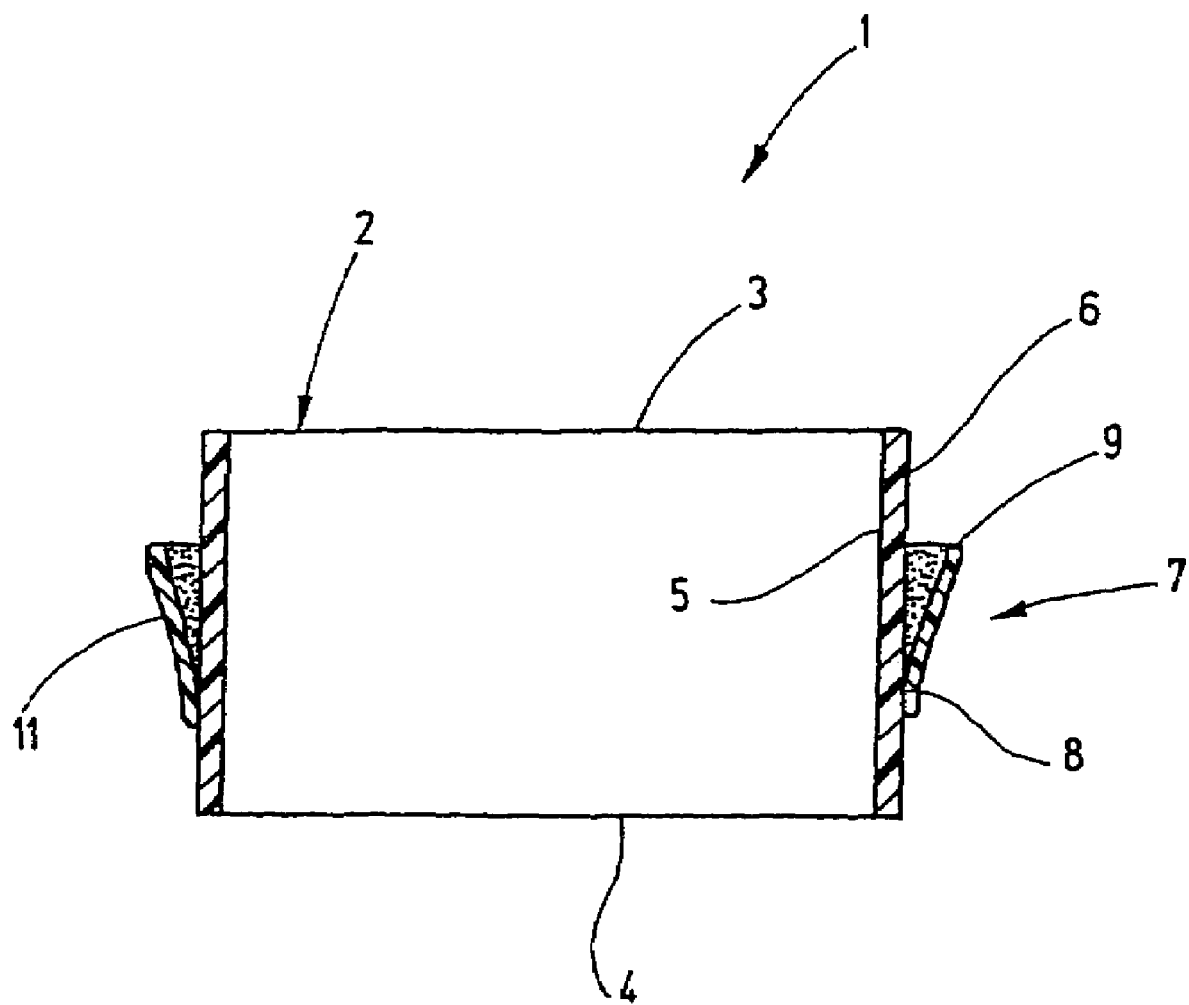
FIG. 1 is a longitudinal section of a first illustrative embodiment of a seal according to the invention.

In a schematic manner, FIG. 1 shows a seal 1 designed to seal off a residual limb (not shown) relative to the inside volume of a prosthetic socket (not shown) for the purpose of keeping the socket against the residual limb by means of a partial vacuum, i.e. to enhance its affixation to the residual limb.

The seal 1 comprises a cuff-like base 2 having a proximal end face 3, a distal end face 4, and an inside surface 5 and an outside surface 6.

The cuff-like base is tubular in the broadest sense and is formed of an air tight, elastically stretchable material. The diameter of said base 2 is selected in a manner that it may be properly seated on a residual limb while being very minimally prestressed. A peripheral sealing lip 7 is affixed on the outside surface 6 of the base 2 and comprises a root 8 and a sealing edge 9 extending at least in part diagonally away from said root. The sealing lip 7 also is shaped like an annulus peripherally surrounding the outside surface 6 of the base 2.

The root 8 is hermetically bonded to the outside surface 6.

The bonding area also constitutes a peripheral and closed ring and only runs in the longitudinal direction of the base 2 over a small fraction of the height of the sealing lip 7 in the embodiment of FIG. 1. As a result, a cross-sectionally conical annular gap may extend above the bonding site of the root 8 between the outside surface 6 and the sealing lip 7. An annular filler element or spacer 11 made of an open-cell foam material is preferably located between the side of the sealing lip 7 facing the outside surface 6 and this latter surface in order to constrain the said annular gap. The ring has a cross-sectionally conical structure and is inserted in a way that its narrow end points toward the root 8.

The sealing edge 9 is kept a distance from the outside of the of the base 6 by the annular spacer 11. The annular gap extends between the outside surface 6 and the radially inward side of the sealing lip 7 so as to be permanently vented by the external atmosphere.

By means of this annular and conical spacer 11, said gap also is maintained even when the base 2 is peripherally enlarged. The radial widening of the base 2 is transmitted by the spacer 11 to the sealing lip 7 and hence also to the sealing edge 9.

Figure 2:
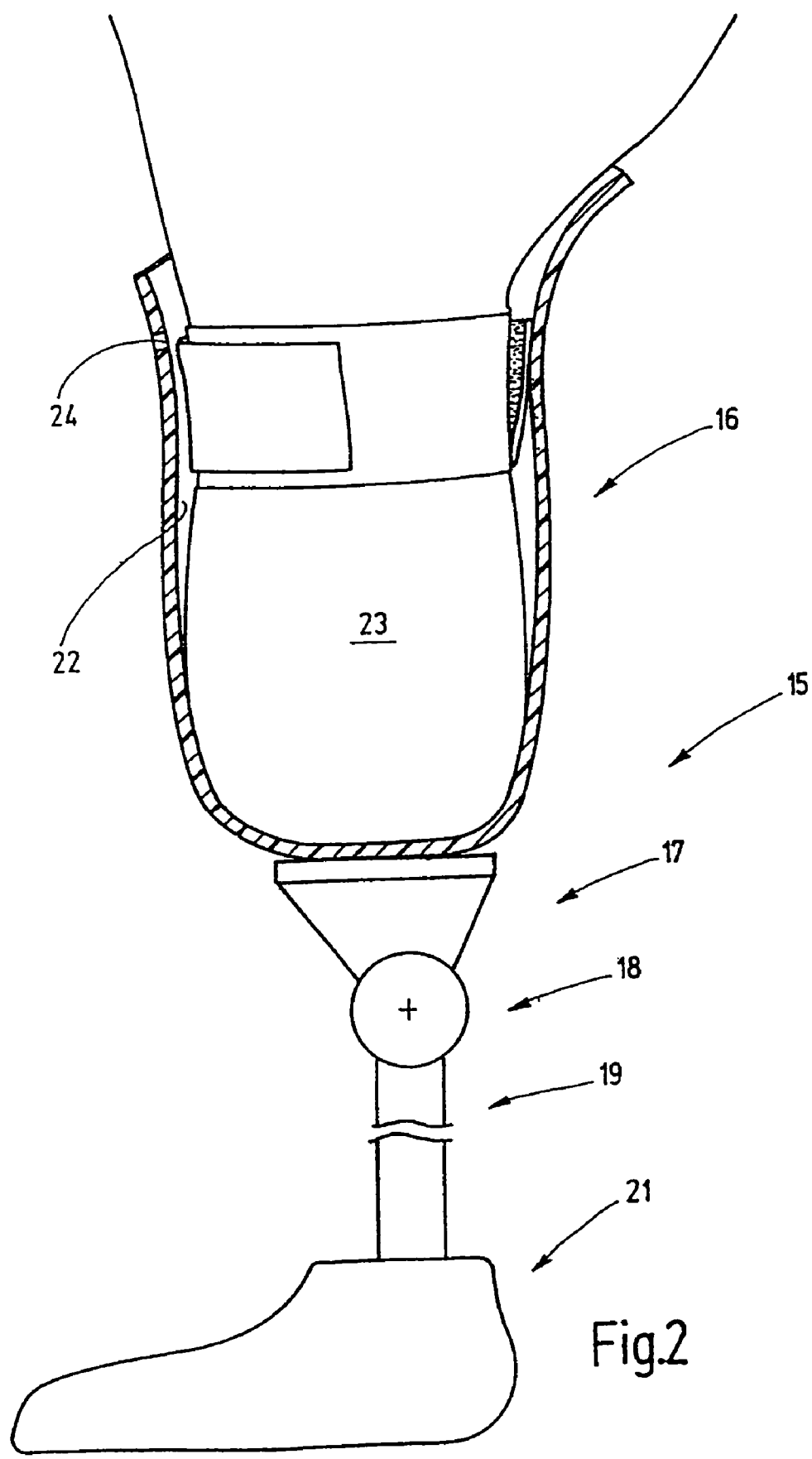
FIG. 2 shows the configuration of the seal of the invention in a prosthetic socket.

FIG. 2 shows the new seal 1 in use.

FIG. 2 in a simplified manner shows an above-the-knee prosthesis 15 which comprises a cup-shaped prosthetic socket 16, an adapter 17, an artificial knee-joint 18, an artificial lower leg 19 and an artificial foot 21.

The prosthetic socket 16 is hermetically sealed at its distal end and is fitted with an inside wall surface 22 which is smooth at least in some areas.

During use, the seal 1 shown in FIG. 1 is slipped over the above-the-knee residual limb in a manner such that the sealing lip 9 extends proximally and the base 8 is located distally on the residual limb 23. Next the patient by his/her above-the-knee residual limb 23 enters the cup-shaped prosthetic socket 16 until the residual limb can proceed no deeper. A valve (not shown) assures that the air in front of the residual limb 23 escapes from the prosthetic socket 16.

In its operational position, the sealing edge 9—or an axial area beginning at the sealing edge 9 and running some distance in the direction of the root 8—will rest against the inside wall surface 22 of the prosthetic socket 16. This prosthetic socket 16 is smooth, at least in this strip-shaped region where it cooperates with the sealing lip 7, in order to attain the desired sealing effect.

The annular spacer 11 assures that the sealing edge 9 constantly rests against the inside wall surface 22. Moreover, on account of its open cell nature, the spacer provides assurance that the gap between the sealing lip 7 and the base 2 will be ventilated by the external ambient atmosphere.

In the drawing it is assumed that the prosthetic socket 16 is sufficiently wide above the seal 1 that, above this seal 1, the patient's tissue will not rest everywhere against the inside socket wall 22 and will not hamper ventilating of the gap between the sealing lip 7 and the base 6.

If such risk were expected, then a borehole 24 may be provided just above the expected position of the sealing edge 9 to act as a pressure balancing duct and optionally to communicate with several grooves the widths of which would be selected to be small enough so they could not be filled by the tissue of the residual limb 23. The positive ventilation of the open-cell spacer 11 would take place through such grooves.

When the prosthetic socket is exposed to a force tending to pull the prosthetic socket 16 off the residual limb 23, there will occur a more or less marked partial vacuum in the distal space between the sealing lip 9 and the base of the prosthetic socket 16. Said partial vacuum acts on the outside of the sealing lip 7, while the inside or back side of the sealing lip 7, namely the side facing the base 2, is ventilated by atmospheric pressure. As a result there is a pressure gradient across the sealing lip 7 such that, as the partial vacuum increases, the compression of the sealing lip 7 against the wall inside surface 22 of the prosthetic socket 16 also increases. The compression is approximately proportional to the pressure difference across the sealing lip.

Thus, contrary to the prior art, where the pressure gradient across the sealing lip extends in the opposite direction and tends to detach the sealing lip as it increases, that is, as the pressure decreases; with the present invention, the sealing lip is increasingly compressed more and more against the inside wall surface 22 of the prosthetic socket 16 as the suction force increases in the socket beneath the seal.

The normal prestressing force by which the sealing edge 9 is forced against the inside wall surface 22 has no practical effect on the air tightness of the seal in the presence of high partial vacuum, that is with a high removal force.

In order to remove the above-knee prosthesis 15, the patient conventionally activates a valve on the prosthetic socket 16 in order to aerate the space below the seal 2 to enable extracting the residual limb 23 out of the prosthetic socket 16.

The seal 2 of the invention is described above with respect to an above-knee prosthesis. It is clear however that the seal 2 also may be used with prostheses used for residual limbs containing little soft tissue, for instance below-knee prostheses. The spacer 11, which also assures back venting of the sealing lip 7, simultaneously also operates as a balancing component between the residual limb cross-section at the level of the seal 2 and the inside cross-section of the respective prosthetic socket at that location.

Even those suction sockets which are comparatively large relative to the residual limb can still be affixed firmly and reliably when using the new seal 2. Such condition arises when a prosthesis is fitted directly following amputation. The residual limb atrophies with time, becoming too large and losing an air tight condition. By using the new seal 1, the prosthesis again may be reliably affixed.

The embodiment shown in FIG. 2 assumes that the seal 1 is seated directly on bare skin.

To attain adequate air tightness, a less flexibly adapting base requires either a comparatively large prestressing force, or this base 2 must be made elongated. The radial prestressing force may be reduced in a base 2 which is long as seen in the residual limb's longitudinal direction.

Instead of pulling the seal 1 directly on the bare skin, it may also and obviously be set on the outside of an appropriate liner which shall be air tight in the region of the seal 1.

Figure 3:
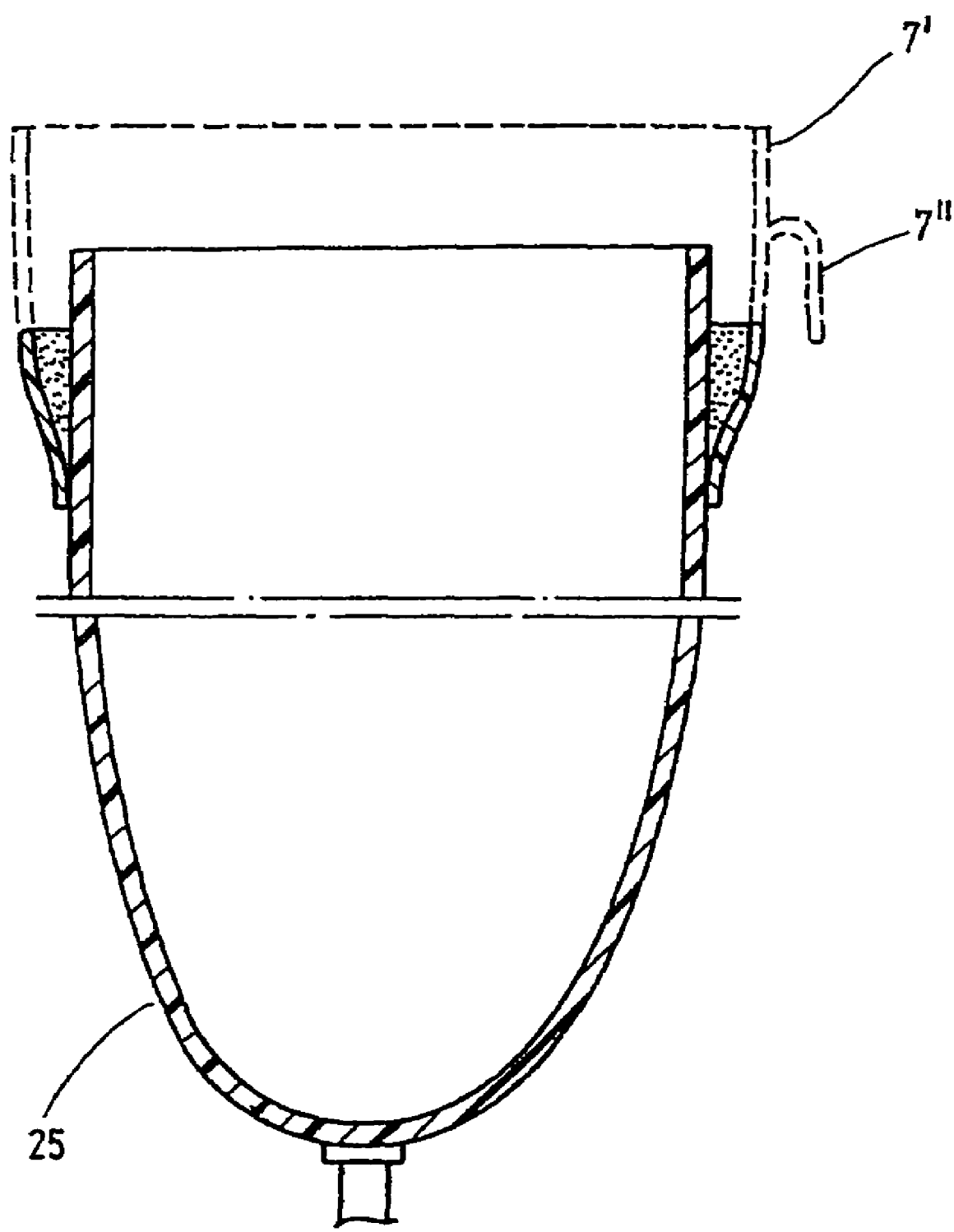
FIG. 3 is a longitudinal section of a liner fitted with the seal of the invention.

FIG. 3 shows another embodiment of the seal 1 of the invention. In this design the base constitutes a liner 25 in the form of a conventional suction sleeve liner. The sealing lip 7 is adhesively bonded to the outside of the liner 25 at a distance from its distal end. The connection between the liner 25 and the sealing lip 7 assumes the same form as already comprehensively discussed above in relation to FIG. 1. A repeat of this description is therefore unnecessary.

The sealing lip 7 of the embodiment shown in FIG. 1 runs axially in such manner that it is entirely contained within the prosthetic socket 16 when the prosthesis 15 is worn.

FIG. 3 shows in dashed lines a sealing lip 7' which normally projects beyond the proximal end of the liner or of the prosthetic socket 2. When in use, it will be folded outwardly over the proximal rim of the prosthetic socket 2, back towards itself as indicated in FIG. 3 by 7". In some cases the spacer 11 may be eliminated from such a configuration because the width of the insertion aperture of the prosthetic socket radially pulls the sealing lip 7 from the liner 25 and thus provides the required back venting.

The means back venting the sealing lip 7 virtually consists in the proximal extension of the sealing lip 7 that folds over of the proximal rim of the prosthetic socket.

Figure 4:
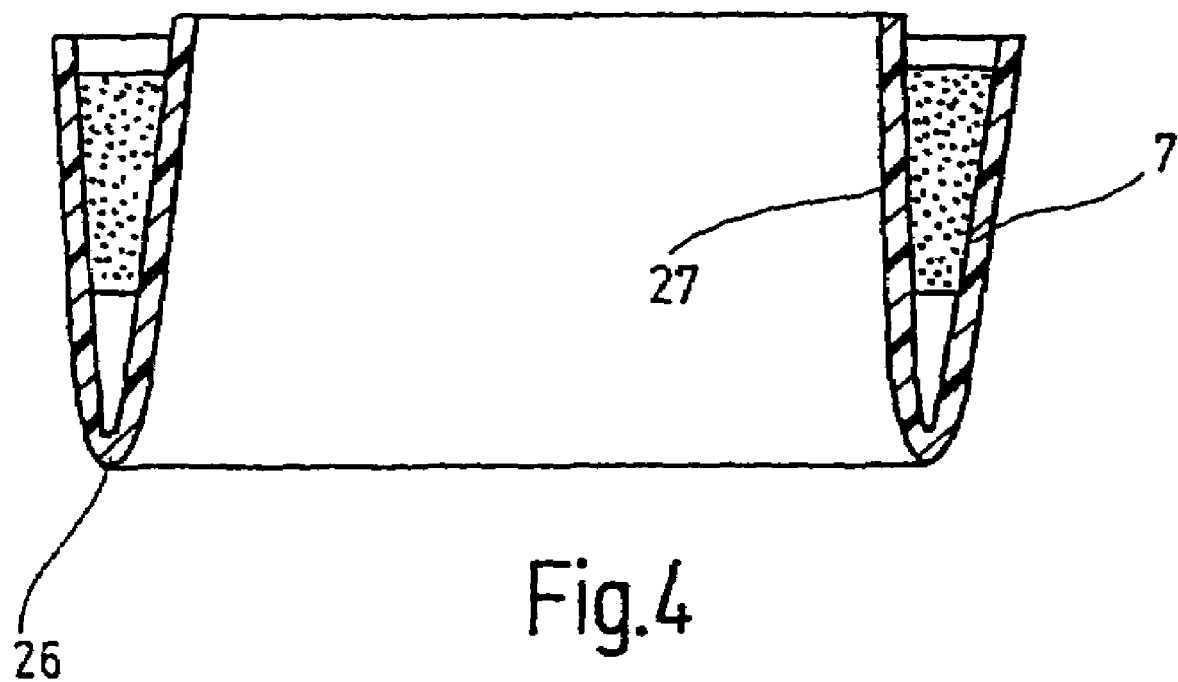
FIGS. 4, 5 are each a longitudinal section of a further embodiment of the seal of the invention.

FIG. 4 illustrates a very simple design of a cuff-like seal. The seal 1 in this case consists of a plain soft tubular segment which is folded on itself at a fold line 26. The fold line 26 simultaneously acts as the root of the external sealing lip 7 and allows subtending an inner sealing lip 27 having the same material properties as the sealing lip 7. The spacer 11 is inserted in the manner already described above between the two sealing lips 7 and 27.

In this respect the fold 26 may be considered as both the root of the sealing lip 7 and the root of the sealing lip 27, that is the same as the base 2. The air tightness provided by the sealing lip 27 relative to the residual limb is the same as described above in relation to the sealing lip 7.

The embodiment of FIG. 4 offers the advantage of especially simple construction.

To preclude the sealing lips 7 and 27 from shifting axially relative to one another, they may be locally bonded adhesively near the fold 26.

Figure 5:
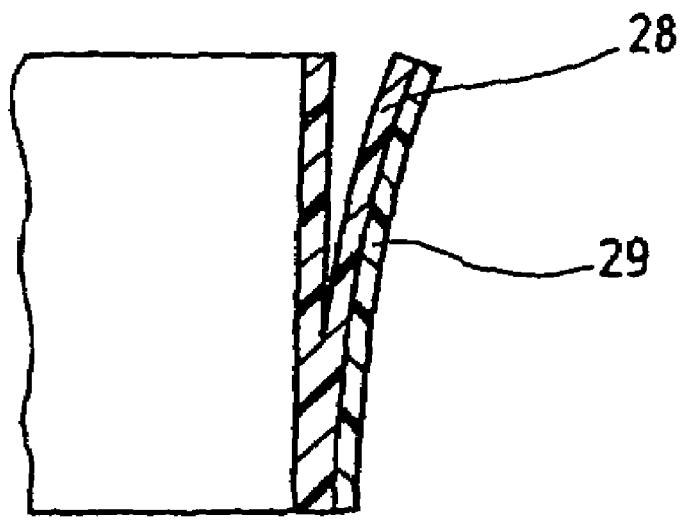

Lastly FIG. 5 shows a seal 1 consisting of a soft tubular base 2 the wall of which is slightly slit open axially. The result is an external sealing strip 28. A second soft outer tubular element 29 is adhesively bonded or vulcanized on the outside of the tubular support, after having been axially stretched before said bonding or vulcanization. As soon as the connection zone has cured, the externally applied force is removed and the outer tube element 29 is cut to the length of the inner support 2. The outer tube 29, being axially prestressed, will tend to bend the strip 28 radially outward. The inner portion of the slit region acts like the inner sealing lip 27 of the embodiment mode of FIG. 4. Venting of the rear side of sealing lip 28 does not require a separate spacer, as shown.

A prosthetic socket seal comprises at least one radially external sealing lip which jointly with a base subtends an annular gap. Said annular gap is vented on a proximal side by the external atmosphere and as a result a pressure gradient is created at the sealing lip, whereupon said gradient will impose a larger compression of said sealing lip against the prosthetic socket when a partial vacuum is applied on a distal side of the sealing lip.

The invention claimed is:

1. A seal for sealing a distal portion of a residual limb within a cup-shaped air tight prosthetic socket comprising:
   a base having proximal and distal ends adapted to be pulled onto a residual limb and to enclose at least a portion of a residual limb peripherally;

at least one sealing lip having a root and a flexibly compliant sealing edge that is spaced from the root and is arranged so as to hermetically rest against an inner wall area of a prosthetic socket and which is affixed by its root to the base;

said sealing lip open to ambient air between its connection with the base and its sealing edge;

said lip extending along a longitudinal direction of the base from the distal end towards the proximal end thereof and diagonally diverging therefrom at least in part in a direction towards the proximal end of the base;

wherein the base and sealing lip are annular.

2. The seal as claimed in claim 1, wherein the base comprises at least a second sealing lip which comprises a second sealing edge that is spaced from the root and is configured to hermetically rest against a residual limb, and wherein the second lip extends peripherally and continuously to enable the second sealing lip to enclose a residual limb, and further wherein the second sealing lip is affixed by its root to said base.

3. The seal as claimed in claim 1, wherein said sealing lip is elastically stretchable at least in a direction parallel to the sealing edge.

4. The seal as claimed in claim 3, wherein when the seal is in an operational position on a residual limb, the sealing edge of the sealing lip extends toward a proximal end of a residual limb.

5. The seal as claimed in claim 1, wherein the sealing lip is made of a material that may elastically closely conform to a contour.

6. The seal as claimed in claim 1, wherein sealing lip contains magnetized ferromagnetic particles.

7. The seal as claimed in claim 1, wherein the base comprises a prosthetic suction liner which is air tight at least in the vicinity of the root of the sealing lip.

8. The seal as claimed in claim 1, wherein the base comprises a cuff which is adapted to engage a residual limb in an air tight manner at least in the region of the root.

9. The seal as claimed in claim 1, including a venting device comprising a spacer located between the base and the sealing lip, said spacing maintaining the area between the base and the sealing lip open to ambient air.

10. The seal as claimed in claim 9, wherein the spacer is resiliently compressible.

11. The seal as claimed in claim 9, wherein the spacer is made of open-cell foam.

12. The seal as claimed in claim 9, wherein the spacer runs peripherally along the sealing lip at least over nearly a full length of the seal.

13. The seal as claimed in claim 1, wherein the sealing lip is configured in a manner to form a bend pointing away from the residual limb whereby, in its operational position, the sealing edge of the sealing lip subtends a cross-sectional surface which is larger than that subtended by the root of the sealing lip.

14. The seal as claimed in claim 1, wherein the sealing lip has a length measured between the root and the sealing edge such that said lip may be outwardly folded over itself.

15. A prosthetic socket using a seal as defined in claim 1.

16. The prosthetic socket as claimed in claim 15, wherein the seal contains magnetized or unmagnetized ferromagnetic particles in its socket wall at least in the region which is opposite the sealing lip of the seal.

* * * * *